US009498337B2

(12) United States Patent
Wang et al.

(10) Patent No.: US 9,498,337 B2
(45) Date of Patent: Nov. 22, 2016

(54) INTERVERTEBRAL IMPLANT

(71) Applicant: METAL INDUSTRIES RESEARCH & DEVELOPMENT CENTRE, Kaohsiung (TW)

(72) Inventors: Wei-Ching Wang, Kaohsiung (TW); Meng-Xiu Wu, Tainan (TW); Fu-Shan Wang, Taichung (TW); Tzyy-Ker Sue, Kaohsiung (TW); Wei-Te Chen, Changhua County (TW); Wei-Jen Shih, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 340 days.

(21) Appl. No.: 14/139,822

(22) Filed: Dec. 23, 2013

(65) Prior Publication Data
US 2015/0173905 A1 Jun. 25, 2015

(51) Int. Cl.
*A61F 2/44* (2006.01)
*A61F 2/30* (2006.01)
*A61L 27/58* (2006.01)
*A61L 27/42* (2006.01)
*A61L 27/56* (2006.01)

(52) U.S. Cl.
CPC ............ *A61F 2/3094* (2013.01); *A61L 27/425* (2013.01); *A61L 27/56* (2013.01); *A61L 27/58* (2013.01); *A61F 2/4455* (2013.01); *A61F 2002/3093* (2013.01); *A61F 2002/30968* (2013.01); *A61L 2430/38* (2013.01)

(58) Field of Classification Search
CPC ...... A61F 2/3094; A61F 2/44; A61F 2/4455; A61F 2/446; A61F 2/4465; A61F 2/447; A61F 2/46; A61F 2/4601; A61F 2/4603; A61F 2/4611; A61F 2002/30968; A61F 2002/4475; A61F 2002/448; A61F 2002/4485; A61F 2002/449
See application file for complete search history.

(56) References Cited

U.S. PATENT DOCUMENTS

| 4,882,196 | A | * | 11/1989 | Shimamune | ........ | A61F 2/30767 427/2.27 |
| 4,960,426 | A | * | 10/1990 | Atsumi | ................ | A61C 8/0012 501/1 |
| 5,890,268 | A | * | 4/1999 | Mullen | .................... | A61L 27/04 228/120 |
| 6,709,739 | B1 | * | 3/2004 | Mullen | .................... | A61L 27/04 428/313.9 |
| 8,623,026 | B2 | * | 1/2014 | Wong | ................. | A61B 17/1703 29/592 |
| 8,710,114 | B2 | * | 4/2014 | Rusin | ................... | A61K 6/0017 106/35 |
| 2004/0078087 | A1 | * | 4/2004 | Kim | ........................ | A61L 27/56 623/23.56 |
| 2005/0123672 | A1 | * | 6/2005 | Justin | .................... | A61C 8/0012 427/2.26 |
| 2006/0177379 | A1 | * | 8/2006 | Asgari | ............. | A61K 47/48992 424/9.3 |
| 2006/0188542 | A1 | * | 8/2006 | Bobyn | ................. | A61C 8/0013 424/423 |
| 2007/0003753 | A1 | * | 1/2007 | Asgari | .................... | A61L 27/28 428/315.5 |
| 2007/0282449 | A1 | * | 12/2007 | de Villiers | ............ | A61F 2/4425 623/17.15 |
| 2007/0287027 | A1 | * | 12/2007 | Justin | .................. | A61F 2/30767 428/666 |
| 2008/0175885 | A1 | * | 7/2008 | Asgari | ................ | C22C 33/0257 424/426 |
| 2008/0177378 | A1 | * | 7/2008 | Asgari | .................. | A61L 27/427 623/1.38 |
| 2008/0213611 | A1 | * | 9/2008 | Asgari | .................... | A61L 27/04 428/566 |

(Continued)

*Primary Examiner* — Christian Sevilla
*Assistant Examiner* — Eric S Gibson
(74) *Attorney, Agent, or Firm* — Chun-Ming Shih

(57) ABSTRACT

An intervertebral implant, particularly an intervertebral implant comprising local degradable hydroxyl apatite/metal block and based on a support mounting model of porous hydroxyl apatite with metal powders held for sintering and molding, guides osseous tissues to grow in porous metal and is steadily merged in upper and lower bones when the implanted hydroxyl apatite is gradually degraded in a certain period.

2 Claims, 4 Drawing Sheets

(56) References Cited

U.S. PATENT DOCUMENTS

| | | | | |
|---|---|---|---|---|
| 2009/0276056 | A1* | 11/2009 | Bose | A61L 27/12 623/23.72 |
| 2010/0016989 | A1* | 1/2010 | Lyngstadaas | A61F 2/28 623/23.72 |
| 2010/0137990 | A1* | 6/2010 | Apatsidis | A61L 27/56 623/17.16 |
| 2010/0185299 | A1* | 7/2010 | Nies | A61L 27/04 623/23.53 |
| 2010/0324564 | A1* | 12/2010 | Bjursten | A61B 17/7095 606/92 |
| 2011/0082564 | A1* | 4/2011 | Liu | A61F 2/28 623/23.72 |
| 2011/0142940 | A1* | 6/2011 | Leguen | A61K 9/0024 424/489 |
| 2011/0266265 | A1* | 11/2011 | Lang | A61F 2/30756 219/121.72 |
| 2012/0183429 | A1* | 7/2012 | Liu | A61F 2/28 419/2 |
| 2012/0265167 | A1* | 10/2012 | Simonson | A61B 17/707 604/506 |
| 2013/0210953 | A1* | 8/2013 | Kilway | A61K 6/0052 522/36 |
| 2014/0004207 | A1* | 1/2014 | Leguen | A61K 9/0024 424/602 |
| 2014/0272418 | A1* | 9/2014 | Jung | C03C 4/0007 428/410 |
| 2015/0173905 | A1* | 6/2015 | Wang | A61L 27/58 623/17.16 |
| 2015/0223938 | A1* | 8/2015 | Tiainen | A61L 27/06 623/23.51 |
| 2015/0245899 | A1* | 9/2015 | Lyngstadaas | A61L 27/06 623/23.55 |
| 2015/0352247 | A1* | 12/2015 | Jie | A61L 27/10 424/426 |

* cited by examiner

INTERVERTEBRAL IMPLANT

BACKGROUND OF THE INVENTION

1. Field of the Invention

The present disclosure relates to technology for a medical implant and specially a local degradable porous intervertebral implant which is made from degradable hydroxyl apatite and metal block and steadily merged in upper and lower bones during osteoconduction and bone regeneration.

2. Description of the Prior Art

The intervertebral fusion surgery is known for "spinal fusion" linking two opposing vertebrae from which an intervertebral disc has been removed. In general, the intervertebral fusion surgery is used to treat spinal lesions such as spinal degeneration and slipped disc, each of which causes persistent backache, sciatica or leg weakness. The intervertebral fusion surgery is also an important part of a spinal deformation surgery for scoliosis, spondylolisthesis, and spine trauma.

As one substance to repair osseous tissues, an implant which features biological absorption in addition to its supporting capability will be ideal in practice. An existing spinal fusion device disclosed in U.S. Pat. No. 5,645,598 consists of a metal framework and bio-absorbable materials therein. Embedded between two opposing vertebrae for recovery of osseous tissues, the implant which has insufficient hardness and volume less than vertebrae themselves may sink and damage osseous tissues between opposing vertebrae wearing each other, particularly end planes of vertebrae.

Moreover, most existing supports made from biodegradable polymers for tissue engineering technology belong to a porous structure infiltrated by living cells usually taken from a patient's body during cell culture. Some time after, the support in which cells grow will be implanted in an animal losing immunocompetence (e.g., rat) or a patient (e.g., patient's subcutaneous tissues for subsequent operation). In the next few weeks or months, the cells relying on nutrients supplied by the animal or the patient propagate quickly but the support are dissolved and absorbed. Finally, the implant (real osseous tissues) can be removed from the animal or the patient's subcutaneous tissues and further planted in an injured area to be treated. The above descriptions are presented in U.S. Pat. Nos. 6,139,578, 6,200,606, 5,306,303 and 6,132,463.

A bio-absorbable support with abundant pores inside for tissue engineering technology will be a fine material. For example, porous calcium phosphate cement with pore-forming agents as shown in Patent No. CN 119346A are made of ordinary calcium phosphate cement and pore-forming agents containing sparingly soluble salt, acid salt, basic salt or surfactant or a mixture thereof. However, the calcium phosphate cement classified as bone cement without fixed form is characteristic of poor mechanical strength and incompetent for bone fusion independently.

Another example is a technology method for producing porous magnesium/hydroxyl apatite as shown in Patent No. CN 101099873A. The method is intended to create porous hydroxyl apatite with hydroxyl apatite powders and magnesium powders mixed proportionally and experiencing cold press molding and sintering for vaporizing magnesium. However, the problem of poor mechanical strength still exists in porous hydroxyl apatite with magnesium removed at high temperatures.

A further example is porous degradable magnesium alloy bone scaffold material containing HA (hydroxyl apatite) nano powders as shown in Patent No. CN 101797400A. The porous degradable magnesium alloy bone scaffold material is made from magnesium powders with a trace of refined zinc crystalline grains (magnesium-zinc alloy, 50 to 80%), HA nano powders (10 to 20%) and pore-forming agents (10 to 30%). However, the problem of poor mechanical strength still exists in porous hydroxyl apatite with magnesium removed at high temperatures.

Furthermore, the conventional porous hydroxyl apatite (HA) materials sintered at high temperatures (>1000° C.) feature insufficient micro-sized or nano-sized pores and are difficultly absorbed by a living body. In the other hand, the disadvantages of conventional biodegradable polymers for bone scaffolds are weak mechanical strength and fast dissolution rate. It can be seen from above descriptions that a porous metal material for medical purposes which facilitates osteoconduction, light weight and biological combination should be developed.

Having considered drawbacks derived from conventional porous metal materials for osteoconduction, the inventor studied continuously to develop an intervertebral implant in the present disclosure.

SUMMARY OF THE INVENTION

The object of the present disclosure is to provide an intervertebral implant based on local degradable hydroxyl apatite/metal block which guides osseous tissues to be attached in a porous metal structure and makes the implant steadily merged in upper and lower bones in the course of degradation of the hydroxyl apatite implanted in a human body.

The other object of the present disclosure is to provide an intervertebral implant as a high-molecular degradable material or compound which is made from ceramic or metal material and refers to the bionics principle for satisfactory performance and structure and an adjustable degradation rate.

The further object of the present disclosure is to provide an intervertebral implant as an implantable support featuring cellular biological behaviors and culture efficiency and appropriately fitting, merging and repairing cavities in bones.

The yet other object of the present disclosure is to provide a biocompatible intervertebral implant characteristic of neither cytotoxicity out of culture in vitro nor rejection of a bone in which the intervertebral implant is embedded.

The yet still other object of the present disclosure is to provide an intervertebral implant characteristic of a three-dimensional porous structure and greater internal surface areas in favor of implantation and adhesion of cells, infiltration of nutrients, and discharge of metabolite.

The yet still further object of the present disclosure is to provide an intervertebral implant characteristic of good surface activity which facilitates adhesion of cells, creating nice microenvironment for proliferation of cells.

An intervertebral implant to realize the above purposes is made from porous hydroxyl apatite as a support mounting model in which metal powders are filled for development of the intervertebral implant based on local degradable hydroxyl apatite/metal block in a sintering and molding process as follows:

Step a, mixing: Biodegradable material and adhesive liquid for degradation in a human body are mixed and become a moderate viscous liquid;

Step b, adhesion: The moderate viscous liquid adheres to surfaces and/or cavities of a porous high-molecular support;

Step c, drying and molding: The porous high-molecular support with the moderate viscous liquid attached is dried so that the moderate viscous liquid securely coated on the porous high-molecular support's surfaces and/or cavities clings to original topography of the surfaces and/or cavities;

Step d, sintering and removal: A porous biodegradable support is developed after the high-molecular support and the adhesives are removed during a sintering process in an atmosphere furnace; and Step e, filling and sintering: Metal powders are filled in the porous biodegradable support as a support mounting model and heated in a high-temperature vacuum sintering process for development of the intervertebral implant in which the biodegradable support and the metal powders are bond to each other.

According to the above technical measures, the intervertebral implant is characteristic of good biocompatibility, osteoconduction and biodegradation due to effect of hydroxyl apatite. Based on hydroxyl apatite/metal block, the lifeless intervertebral implant will be gradually dissolved and biodegraded in a certain period and replaced by newborn living osseous tissues. Moreover, the embedded intervertebral implant based on hydroxyl apatite/metal block is mechanically bonded to a person's bones for creating extra added values of the product and economic efficiency by guiding osseous tissues to grow in cavities of bones but obstructing intrusion of soft tissues.

DETAILED DESCRIPTION OF THE PREFERRED EMBODIMENT

Figure 1:
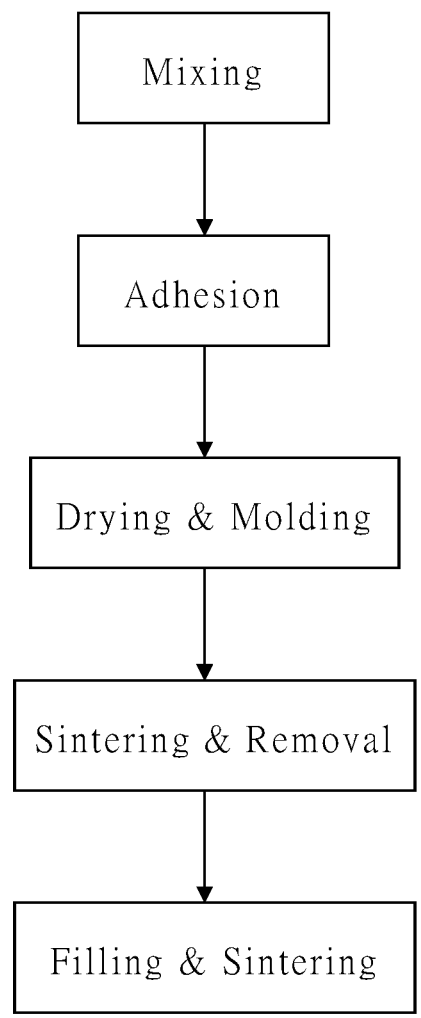
FIG. 1 is a flow diagram briefly illustrating manufacture of an intervertebral implant in the present disclosure.

Please refer to FIG. 1 which illustrates an intervertebral implant in the present disclosure is made from metal powders and biodegradable material. In the present disclosure, the biodegradable material evolves a plurality of interconnected pores after experiencing a sintering process; the metal powders are bonded to the biodegradable material after filled in the interconnected pores and sintered. Held in the intervertebral implant, the biodegradable material, which depends on body fluid dissolution and cell-mediated biodegradation to join reconstruction of local osseous tissues or remote osseous tissues with the implant embedded, is gradually discharged by the metabolic system and allows a defective part to be replaced by newborn osseous tissues thoroughly. Meanwhile, the metal support evolves a permanent support based on osseous tissue engineering support material. Moreover, bio-absorbable material as a substitute of the biodegradable material is an alternative option based on the identical principle to realize the above purposes.

Figure 2:
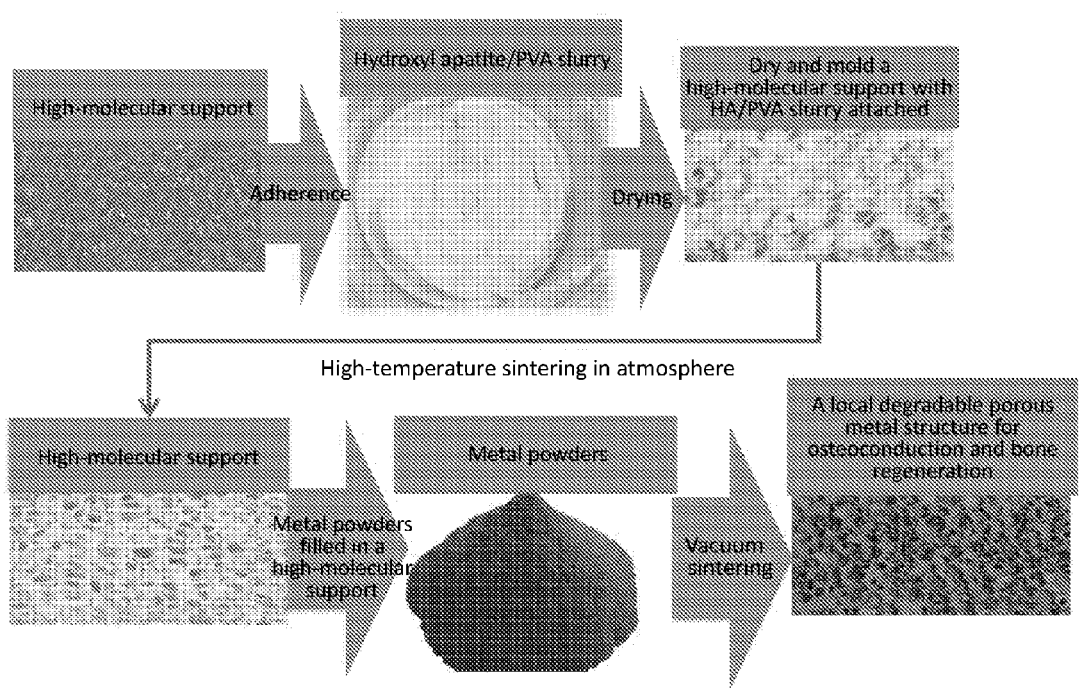
FIG. 2 is a schematic view illustrating steps of manufacturing an intervertebral implant in the present disclosure.
Figure 3:
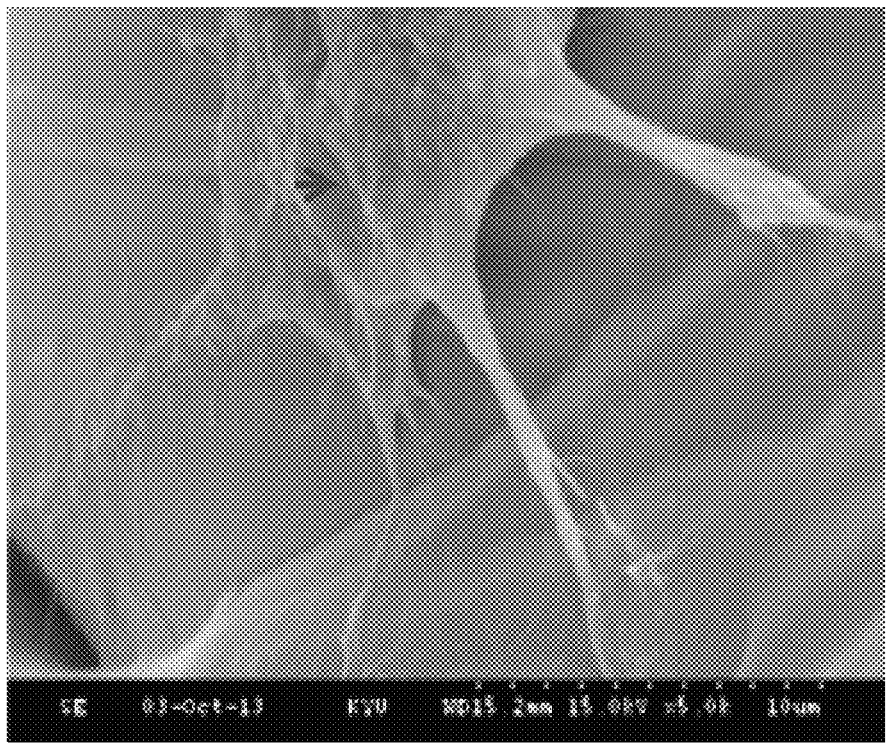
FIGS. 3-6 are photos illustrating normal cells adhering to surfaces of a porous metal structure.
Figure 4:
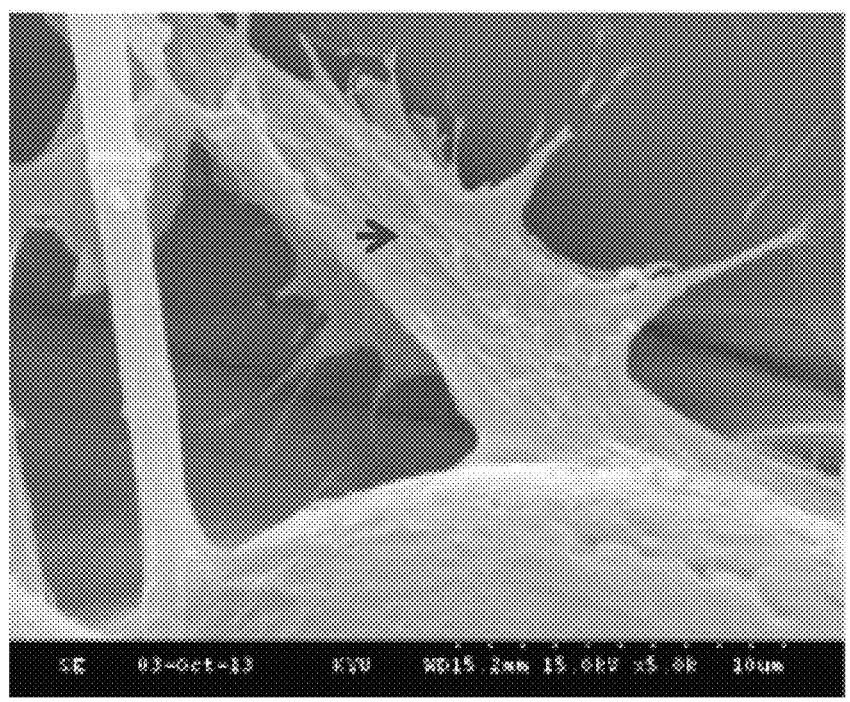
Figure 5:
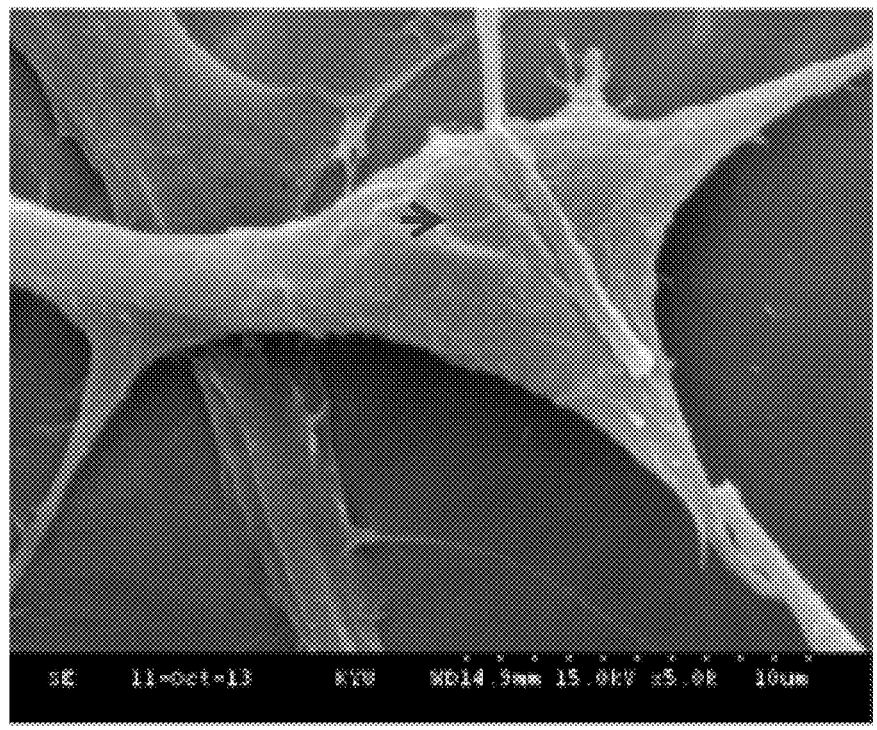
Figure 6:
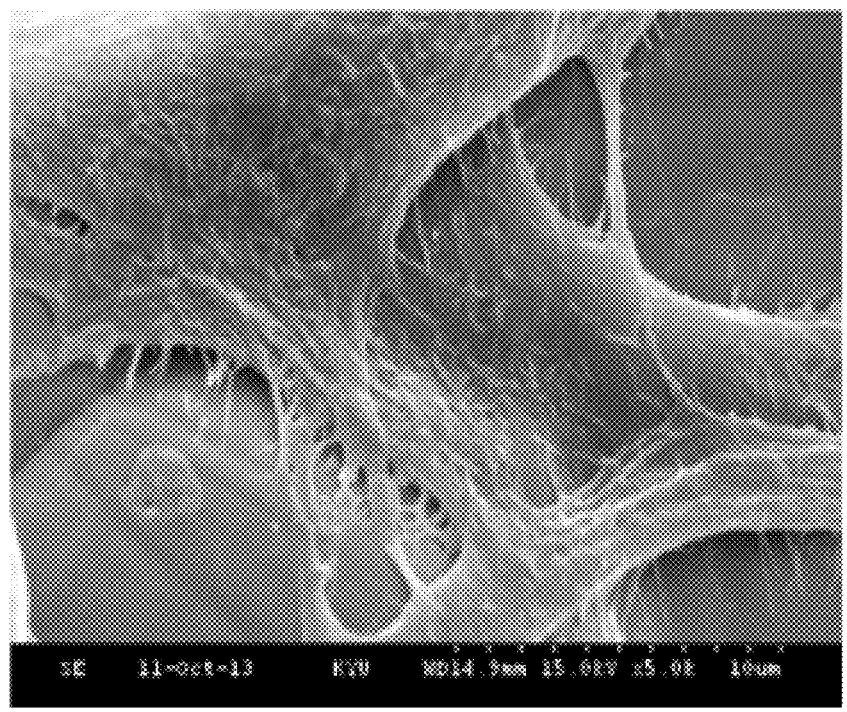

Please refer to FIGS. 1 and 2 again which illustrate manufacture of the intervertebral implant comprises steps as follows. Step a, mixing: Biodegradable material and adhesive liquid for degradation in a human body are mixed at temperatures between 1100 and 1300° C. for 10 to 60 minutes and become a moderate viscous liquid. In the mixed liquid, the biodegradable material and the adhesive can be hydroxyl apatite and polyvinyl acetate (PVA or PVAc, an elastic synthetic polymer), respectively; preferably, hydroxyl apatite and polyvinyl acetate in the embodiment are mixed to become hydroxyl apatite/PVA slurry as shown in FIG. 2;

Step b, adhesion: The moderate viscous liquid adheres to surfaces and/or cavities of porous high-molecular supports. As shown in FIG. 2, the high-molecular support made from ceramic or metal material comprises a plurality of cavities;

Step c, drying and molding: The porous high-molecular support with the moderate viscous liquid attached is dried and molded in an oven at temperatures between 50 and 100° C. for 8 to 24 hours. The moderate viscous liquid securely coated on the porous high-molecular support's surfaces and/or cavities will cling to original topography of the surfaces and/or cavities; preferably, the surfaces and/or cavities of the high-molecular support with the hydroxyl apatite/PVA slurry attached still presents a porous structure;

Step d, sintering and removal: A biodegradable material support with a porous structure as shown in FIG. 2 is developed after the high-molecular support and the adhesives are removed during a sintering process in an atmosphere furnace at high temperatures between 1100 and 1300° C.; and Step e, filling and sintering: Metal powders are filled in the porous biodegradable material support which is taken as a support mounting model, that is, a three-dimensional structure with interconnected pores (sizes between 10 μm to 200 μm). The metal powders can be selected from any of titanium, titanium alloy, zirconium, zirconium alloy, tantalum or tantalum alloy or a mixture thereof, each of which is molded in a sintering process, and present uniform metal spheres with granule diameters between 10 μm and 100 μm identical to those of the metal powders before sintering. The high-molecular support with metal powders filled should be heated in a high-temperature vacuum sintering process between 1100 and 1300° C. for 1 to 3 hours for development of the intervertebral implant in which the biodegradable material and the metal powders are bonded to each other. Preferably, a block structure or a porous intervertebral implant in the present disclosure (i.e., a local degradable porous metal structure for osteoconduction and bone regeneration) as shown in FIG. 2 with hydroxyl apatite and metal sintered should be derived from the embodiment.

Based on hydroxyl apatite/metal block in the above preparation method, the intervertebral implant embedded in a human body is effective in gradually growing in cavities of osseous tissues. In the intervertebral implant, the hydroxyl apatite implanted in a human body is a degradable material featuring some material structures as determinant attributes to decide the intervertebral implant's biodegradation. For example, the hydroxyl apatite with a Ca/P ratio of 1.65 to 1.75 keeps apatite's material structure after sintering and contributes to osteoconduction during growth of new bones because of slow degradation in extended implantation time. In the course of slow degradation, the hydroxyl apatite characteristic of a satisfactory osteoconduction effect is able to guide growth of new osseous tissues along and inside the hydroxyl apatite/metal-based intervertebral implant for stable healing and firm mechanical fixing of upper and lower osseous tissues.

In conclusion, the present disclosure as per the above structural design presents preparation of a porous metal structure by which an intervertebral implant based on local degradable hydroxyl apatite/metal block is developed simplifies and facilitates biological attachment because the hydroxyl apatite structure guides osseous tissues to be attached in a porous metal structure and makes the implant steadily merged in upper and lower bones in the course of extended degradation of the hydroxyl apatite implanted in a human body.

In the present disclosure, an intervertebral implant has following advantages compared with the cited references and other prior arts:

Biodegradation: The intervertebral implant based on the hydroxyl apatite/metal block is gradually degraded during growth of new osseous tissues with its structure and functions unaffected.

Plasticity: The intervertebral implant based on the hydroxyl apatite/metal block is machined to be a specific shape, presents certain mechanical strength, and keeps the shape within a certain period for newly developed tissues matching a design contour.

What is claimed is:

1. A method to prepare an intervertebral implant, the intervertebral implant which is made from metal powders and biodegradable material; the intervertebral implant characterized in that said biodegradable material develops a plurality of interconnected pores in a sintering process and said metal powders, which are filled in said interconnected pores, and said biodegradable material are bonded to each other in a sintering process, comprising steps as follows:

Step a, mixing: Biodegradable material for degradation in a human body and an adhesive liquid are mixed and become a moderate viscous liquid;

Step b, adhesion: The moderate viscous liquid adheres to surfaces and/or cavities of a porous high-molecular support;

Step c, drying and molding: The porous high-molecular support with the moderate viscous liquid attached is dried so that the moderate viscous liquid securely coated on the porous high-molecular support's surfaces and/or cavities clings to original topography of the surfaces and/or cavities;

Step d, sintering and removal: A porous biodegradable support is developed after the high-molecular support and the adhesive liquid are removed during a sintering process in an atmosphere furnace; and Step e, filling and sintering: Metal powders are filled in the porous biodegradable support as a support mounting model and heated in a high-temperature vacuum sintering process for development of the intervertebral implant in which biodegradable material and metal powders are bonded to each other.

2. The method to prepare the intervertebral implant according to claim 1, wherein said biodegradable material is hydroxyl apatite which is mixed with said adhesive liquid and sintered for development of said porous biodegradable support comprising said interconnected pores with sizes from 10 μm to 200 μm.

* * * * *